United States Patent [19]

Monnier et al.

[11] Patent Number: 5,145,968

[45] Date of Patent: * Sep. 8, 1992

[54] SELECTIVE MONOEPOXIDATION OF STYRENE, STYRENE ANALOGS, AND STYRENE DERIVATIVES TO THE CORRESPONDING OXIDE WITH MOLECULAR OXYGEN

[75] Inventors: John R. Monnier, Fairport; Peter J. Muehlbauer, Spencerport, both of N.Y.

[73] Assignee: Eastman Kodak Company, Rochester, N.Y.

[ * ] Notice: The portion of the term of this patent subsequent to Jan. 30, 2007 has been disclaimed.

[21] Appl. No.: 394,023

[22] Filed: Aug. 15, 1989

Related U.S. Application Data

[63] Continuation-in-part of Ser. No. 270,332, Nov. 14, 1988, abandoned.

[51] Int. Cl.$^5$ .................. C07D 403/04; C07D 301/10
[52] U.S. Cl. .................................... 546/268; 549/534; 549/536; 549/537
[58] Field of Search ................ 546/268; 549/534, 536, 549/537

[56] References Cited

U.S. PATENT DOCUMENTS

| | | | |
|---|---|---|---|
| 2,404,438 | 7/1946 | Evans | 549/534 |
| 2,992,238 | 7/1961 | Zimmerman | 260/348.5 |
| 4,760,042 | 7/1981 | Armstrong | 549/534 |
| 4,894,467 | 1/1990 | Blum | 549/534 |

FOREIGN PATENT DOCUMENTS 48-40739  6/1973  Japan .................................. 549/537

OTHER PUBLICATIONS

Y. Murakami, et al., *Nippon Kagaku Kaishi*, 11, "Styrene Oxide Synthesis by Vapor-Phase Oxidation of Styrene," pp. 1603–1609 (1977).

*Primary Examiner*—Glennon H. Hollrah
*Assistant Examiner*—Mark W. Russell
*Attorney, Agent, or Firm*—J. Frederick Thomsen; William P. Heath, Jr.

[57] ABSTRACT

Process is disclosed for the slective monoepoxidation of styrene, styrene analogs, and styrene derivatives. Such compounds are contacted with an oxygen-containing gas in the presence of a promoted, optionally supported silver catalyst under defined reaction conditions, thereby selectively producing opoxides in good yield.

6 Claims, No Drawings

SELECTIVE MONOEPOXIDATION OF STYRENE, STYRENE ANALOGS, AND STYRENE DERIVATIVES TO THE CORRESPONDING OXIDE WITH MOLECULAR OXYGEN

This application is a continuation-in-part of Ser. No. 270,332, filed Nov. 14, 1988, now abandoned.

This invention relates to the selective oxidation of styrene and styrene derivatives employing molecular oxygen to produce the corresponding oxide.

BACKGROUND OF THE INVENTION

Epoxides are highly reactive chemical compounds which, as a result of their reactivity, can be used in a wide variety of applications. Unfortunately, due to the reactivity of epoxides, they are often difficult to prepare with high selectivity and in high yields. Ethylene is the only olefin which has been successfully oxidized employing molecular oxygen on a commercial scale to produce an epoxide.

Preferred catalysts employed for the oxidation of ethylene to produce ethylene oxide comprise silver on solid supports. When such catalysts are employed for the oxidation of other olefins such as styrene, epoxides are obtained, if at all, only in low yields and with relatively low selectivity. In addition, significant quantities of various higher oxidation products (up to and including carbon dioxide and water) are obtained.

For example, U.S. Pat. No. 2,992,238 (assigned to the Dow Chemical Company, issued Jul. 11, 1961) indicates that "all attempts to find a catalyst that would allow direct oxidation of higher olefins to epoxide in the same manner that silver catalyst works for ethylene led to failure . . ." (col. 1, lines 22-25). There is then disclosed a particular type of supported silver catalyst useful for oxidation of styrene, which catalyst is prepared by a reduction process using a polyhydric alcohol compound as both a reductant and as an agent for promoting adhesion between molecular silver and the support on which it is deposited. Catalyst preparation, therefore, requires special attention and involves the use of additional chemicals such as diethylene glycol.

Conversions in the range of 3 up to only 13.4 percent are reported for these polyhydric alcohol-prepared catalysts. Selectivities to styrene oxide reported are as low as 47% when higher conversions are achieved, and no higher than 85% at the very low conversion levels. Thus, mediocre performance is obtained employing catalyst which requires special considerations when being prepared.

Japanese Kokai Patent No. Sho 48[1973]-40739 reports an improvement over the disclosure of '238 by using a catalyst obtained by adding large quantities of barium peroxide to silver oxide. Ratios of barium to silver fall in the range of about 0.01:1 up to 1:1. Indeed, the authors indicate that a barium peroxide-free silver catalyst exhibits hardly any styrene oxide-producing activity in a process whereby styrene is oxidized.

While the authors of the above noted Japanese reference indicate that barium peroxide-containing catalyst can produce styrene oxide in an extremely high yield, the examples reveal styrene conversions in the range of about 14 up to 50 mol %, with selectivities in the range of only about 60 mol % at the higher conversion levels, with somewhat higher selectivity, up to 86 mol % at lower conversion levels.

The Japanese authors of the Japanese Kokai reference discussed above have also published a detailed scientific report of their work on the vapor-phase oxidation of styrene to styrene oxide in Nippon Kagaku Kaishi, 1977(11), pp. 1603-1609. This study investigates the affect of catalyst additives such as calcium nitrate, sodium hydroxide, magnesium powder, barium peroxide, tin hydroxide, diphosphorus pentoxide and potassium hydroxide on styrene conversion and selectivity to styrene oxide. The styrene conversions reported fall in the range of 0.1 up to 17% with selectivities to styrene oxide of 50 mol % at high styrene conversion, and up to 78% at the lower conversion levels, with the best performance reported employing the barium peroxide additive.

Alternate routes to styrene oxide and oxides of styrene derivatives include the non-catalytic oxidation of styrene with peroxides. Such processes are not only uneconomical, but are also hazardous due to the large quantities of peroxide required for desirable conversion levels.

It would, therefore, be desirable to be able to catalytically oxidize styrene or styrene derivatives to produce the corresponding oxide directly in high yields and with high selectivity. Such processes would provide large quantities of highly reactive olefin derivatives which would find a wide range of uses, such as for example, as polymer cross-linking agents, as reactive chemical intermediates, as precursors for the production of organic solvents, and the like.

OBJECTS OF THE INVENTION

An object of the present invention, therefore, is to provide a catalytic process for the selective oxidation of styrene, styrene analogs, or styrene derivatives to produce the corresponding oxide in high yield.

This and other objects of the present invention will become apparent from inspection of the detailed description and appended claims which follow.

STATEMENT OF THE INVENTION

In accordance with the present invention, we have discovered that styrene, styrene analogs, and styrene derivatives can be catalytically oxidized to produce a high selectivity of epoxide derivatives thereof by contacting the unsaturated feed with an oxygen-containing gas in the presence of a promoted silver catalyst under defined oxidation conditions. The practice of the present invention makes possible the large scale production of such highly functionalized compounds as styrene oxide, p-fluoro styrene oxide, p-chloro styrene oxide, vinyl pyridine oxide, and the like by employing readily available feedstocks (e.g., styrene).

The only other material consumed during the invention reaction, besides the olefin feedstock, is molecular oxygen. Thus, the invention process is not only economical, but, since the reaction can be run in the continuous mode, it also makes possible the ready preparation of large quantities of these useful chemical compounds.

DETAILED DESCRIPTION OF THE INVENTION

In accordance with the present invention, we have developed a process for the selective monoepoxidation of styrene, styrene analogs, and styrene derivatives, which process comprises contacting the unsaturated feed compound with a sufficient quantity of an oxygen-containing gas so as to maintain the molar ratio of unsaturated compound to oxygen in the range of 0.01 up to 30, in the presence of a promoted silver catalyst at a reaction pressure in the range of 0.1 up to 100 atmospheres and a temperature in the range of about 100° up to 325° C. for a reaction time sufficient to obtain unsaturated compound conversions in the range of about 0.5 up to 75 mole percent.

Styrene compounds contemplated for use in the practice of the present invention are those which satisfy the following structural formula:

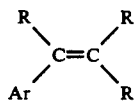

wherein Ar is aryl, substituted aryl, heteroaryl, or substituted heteroaryl having in the range of 5 up to 20 carbon atoms, and each R is independently selected from hydrogen, hydrocarbyl or substituted hydrocarbyl groups, with the proviso that there are no hydrogen atoms allylic to the double bond. Hydrocarbyl groups having in the range of 1 up to 20 carbon atoms are contemplated. Substituted hydrocarbyl groups include alkyl, aryl, alkaryl, aralkyl, cycloalkyl moieties and the like, optionally substituted with substituents such as alkoxy, acyl, acyloxy, amino, aminoxy, and the like.

Exemplary aryl moieties, Ar, include phenyl, pyridyl, naphthyl, anthracenyl, phenanthryl, biphenyl, vinylphenyl and the like.

Substituted aryl moieties contemplated include phenyl or pyridyl rings bearing up to four substituents, so long as none of the substituents have a hydrogen allylic to a double bond. Typical aryl substituents include alkoxy, acyl, acyloxy, amino, aminoxy, halogen, and the like.

Exemplary olefins which satisfy the above structural formula include styrene, divinyl benzene, p-fluorostyrene, p-chlorostyrene, p-vinyl anisole, p-vinyl-N,N-dimethylaniline, stilbine, 4-vinylbiphenyl, 2-vinylpyridine, 4-vinylpyridine, and the like. Styrene is the presently preferred olefin for use in the practice of the present invention because of its ready availability, relatively low cost, and the wide range of possible uses for the epoxide reaction product.

The silver catalyst required for the practice of the present invention can be employed in either supported or unsupported forms.

When a support is employed, the loading level of silver on support typically falls within the range of about 0.5 up to 50 weight percent, calculated as elemental silver and based on the total weight of finished catalyst. Preferably, the loading level of silver on support falls within the range of about 1 up to 30 weight percent elemental silver; with loading levels in the range of about 2 up to 20 weight percent being most preferred.

It is presently preferred to apply the silver to a solid support for efficient use of the expensive silver component. Typical catalyst supports include
silica,
alumina,
silica-alumina,
zeolites,
titanium oxide,
lanthanum oxide,
magnesium oxide,
boron nitride,
boron carbide,
silicon nitride,
silicon carbide,
zinc oxide,
tin oxide,
iron oxide,
calcium oxide,
barium oxide,
strontium oxide,
zirconium oxide,
carbon,
boron phosphate,
zirconium phosphate,
and the like, as well as mixtures of any two or more thereof.

Typically, these solid supports will have a surface area of less than about 50 m$^2$/g. Preferred supports will have a surface area of less than about 10 m$^2$/g and will be neutral or moderately basic in character. Such supports include silica, alumina, titanium oxide, zinc oxide and the like. The presently most preferred supports have surface areas of less than about 1 m$^2$/g, and include alumina, zinc oxide and titanium oxide.

The actual physical form of the catalyst support is not particularly important. While the form of the catalyst support has little effect on catalyst activity, practical considerations such as ease of heat transfer, mass transfer, pressure drop due to fluid flow restrictions, efficiency of gas-liquid-solid contacting, catalyst durability, and the like make the use of defined shapes such as spheres, pellets, extrudates, rings, saddles, and the like preferred.

Promoters employed in the practice of the present invention are selected from at least one promoter selected from the group consisting of:
the salts of alkali metals,
the oxides of alkali metals,
the salts of alkaline earth metals,
the oxides of alkaline earth metals,
excluding barium peroxide, and the like, as well as mixtures of any two or more thereof.

Exemplary salts of alkali metals include sodium nitrate, sodium sulfate, sodium chloride, sodium bromide, rubidium nitrate, rubidium acetate, lithium sulfate, lithium chloride, cesium nitrate, cesium chloride, cesium bromide, and the like; exemplary oxides of alkali metals include sodium oxide, sodium hydroxide, cesium oxide, cesium hydroxide, lithium oxide, lithium hydroxide, and the like; exemplary salts of alkaline earth metals include barium nitrate, barium acetate, calcium nitrate, calcium acetate, calcium chloride, and the like; and exemplary oxides of alkaline earth metals include barium oxide, barium hydroxide, calcium oxide, calcium hydroxide, and the like. Those of skill in the art recognize that the above-recited compounds are merely illustrative of the compounds which are useful as promoters in the practice of the present invention, and that many other compounds which fall within the generic categories set forth above can also be identified and would be expected to also impart enhanced activity and/or selectivity to the catalyst employed in the practice of the present invention.

Of the above compounds, the alkali metal halides and nitrates are most preferred. Exemplary preferred alkali metal compounds include cesium chloride, rubidium chloride, potassium chloride, sodium chloride, sodium bromide, potassium bromide, rubidium bromide, cesium bromide, cesium nitrate, rubidium nitrate, potassium nitrate, sodium nitrate, and the like.

The quantity of promoter employed can vary widely. Generally, catalyst can be treated with in the range of 0.001 up to 10 weight %, based on the total weight of catalyst, including support (if employed), of at least one of the above-mentioned promoters. The preferred quantity of promoter employed falls within the range of about 0.01 up to 2 wt %, with promoter loadings of about 0.05 up to 1 wt % being most preferred.

Those of skill in the art recognize that catalysts employed in the practice of the present invention can include additional components which may modify catalyst activity and/or selectivity. Such additives may be incorporated into the finished catalyst because their presence aids catalyst preparation, e.g., binders, die lubricants, and the like; or additives may be incorporated as extenders to reduce the cost of catalyst preparation; or additives may be incorporated to extend the operating ranges for reaction temperature and/or pressure; or additives may be incorporated to increase catalyst lifetime under reaction conditions and/or to modify the amounts of catalyst promoters employed to produce enhanced catalyst activity, e.g., organic halides, inorganic halides, acid halides, or elemental halogens. It is recognized, of course, that some additives (e.g., cesium) are suitably employed in very low levels (i.e., milligrams of additive per gram of catalyst); while other additives (i.e., binders, diluents, and the like) are suitably employed at significantly higher levels (i.e., as a significant percentage of the total catalyst weight).

Supported catalysts can be prepared employing techniques well known to those of skill in the art, such as, for example, by precipitation of the active metals on the support, by impregnation, by coprecipitation of support and active metals, by grinding together solid support and active metal(s) in particulate form; and the like. The order in which promoter is incorporated into the catalyst is not critical, i.e., support can be contacted with a silver source, then promoter; or support can be contacted with promoter, then a silver source; or support can be contacted simultaneously with both promoter and a silver source; and other such variations.

Most any source of silver is suitable for use in preparing the catalyst employed in the practice of the present invention. Since a preferred method for preparation of supported catalyst involves impregnation of support with a solution of a silver compound, soluble silver compounds are a presently preferred source of silver. Exemplary compounds are silver nitrate, silver oxalate, silver acetate, and the like. Those of skill in the art recognize that certain organic silver compounds require the addition of ammonia or an amine in order to solubilize the organic silver compound in aqueous medium; thus, the use of such solvation-promoting additives is contemplated in the practice of the present invention.

The process of the present invention is carried out under oxidation conditions, i.e., in the presence of sufficient quantities of an oxygen-containing gas to provide a molar ratio of unsaturated compound to oxygen in the range of about 0.01 up to 30. While greater or lesser quantities of molecular oxygen can be employed, sufficient quantities of oxygen should be provided to insure that undesirably low levels of unsaturated compound conversion do not occur, while excessively high oxygen concentrations should be avoided to prevent the formation of explosive mixtures.

Suitable oxygen-containing gases include air, oxygen-enriched air, substantially purified oxygen, oxygen diluted with inert gases such as $N_2$, Ar, $CO_2$ or $CH_4$, air diluted with inert gases such as $N_2$, Ar, $CO_2$, or $CH_4$, and the like.

Suitable reaction temperatures fall within the range of about 100° up to 325° C. At lower temperatures, the reaction proceeds so slowly as to be impractical, while at higher temperatures undesirable levels of by-products, e.g., carbon dioxide, are obtained. Preferred reaction temperatures fall within the range of about 125° up to 300° C.; with temperatures in the range of about 175° up to 275° C. being most preferred because selectivity to the desired monoepoxide falls off at temperatures significantly above about 275° C. and space-time yields are undesirably low at temperatures below about 175° C.

The reaction pressure can vary within wide ranges, with typical limits of about 0.1 up to 100 atmospheres being chosen primarily as a function of safety, handling, equipment and other practical considerations. Preferably, reaction pressure is maintained in the range of about 1 up to 30 atmospheres.

Reaction times suitable for the practice of the present invention can vary within wide ranges. Generally, unsaturated compound, oxygen and catalyst are maintained in contact for a time sufficient to obtain olefin conversions in the range of about 0.5 up to 75 mole percent. Reaction times sufficient to obtain unsaturated compound conversion in the range of about 5 up to 60 mole percent or higher are preferred for efficient utilization of the reactor capacity.

Those of skill in the art recognize that the actual contact times required to accomplish the desired conversion levels can vary within wide ranges, depending on such factors as vessel size, unsaturated compound to oxygen ratios, the silver loading level on the catalyst, the nature of the catalyst modifiers employed (and their loading levels), the reaction temperature and pressure, and the like.

The invention process can be carried out in either batch or continuous mode. Continuous reaction is presently preferred since high reactor throughput and high purity product is obtained in this manner. The batch mode is satisfactorily employed when high volume of reactant throughput is not required, for example, for liquid phase reactions.

For continuous mode of reaction carried out in the gas phase, typical gas hourly space velocities (GHSV) fall within the range of about 100 up to 30,000 $hr^{-1}$. GHSV in the range of about 200 up to 20,000 $hr^{-1}$ are preferred, with GHSV in the range of about 300 up to 10,000 $hr^{-1}$ being most preferred because under such conditions the most desirable combination of unsaturated feed compound conversion and product selectivities are obtained.

When continuous mode of reaction is carried out in the liquid phase, typical liquid hourly space velocities (LHSV) employed will give contact times analogous to that obtained at the GHSV values given above. Most preferably, LHSV employed will fall in a range so as to produce the most desirable combination of feed olefin conversion levels and high product selectivity.

Recovery of product produced in the practice of the present invention can readily be carried out employing techniques well known by those of skill in the art. For example, where reaction is carried out in the continuous mode, unreacted starting material is initially separated from reaction products; and the desired product then isolated from the resulting product mixture by distillation, crystallization, extraction, or the like. Since the selectivity to the desired epoxide product is generally quite high, there are only small amounts of undesired reaction products from which to isolate the desired product.

The invention will now be described in greater detail by reference to the following non-limiting examples.

EXAMPLE 1

Catalyst Preparation

Catalysts were typically prepared by impregnation of support with a solution of a silver compound and a promoter in 1-2 volumes of solvent relative to the volume of support being treated. Thus, for example, a catalyst containing about 15 wt. % Ag (as determined by neutron activation analysis) on $Al_2O_3$ support was prepared by dissolving 202.3 grams of Kodak silver nitrate in 500 mL of distilled water. Five hundred grams of calcined $Al_2O_3$ ¼" rings having a surface area of 0.43 $m^2/g$, a total pore volume of 0.37 cc (Hg)/gm, a median pore diameter of 7$\mu$, a packing density of 0.80 $g/cm^3$, and a chemical composition (wt %) as follows: $Al_2O_3$—93.1, $SiO_2$—5.6, $Fe_2O_3$—0.3, $TiO_2$—0.1, CaO—0.1, MgO—0.3, $Na_2O$—0.1, $K_2O$—0.1 were added to the silver-containing solution, the mixture tumbled for 30 minutes at 50° C., then water removed under vacuum at 60° C. The resulting pellets were then dried for 30 minutes at 120° C. in a forced air oven. This catalyst is designated as Catalyst D (see Table I). This material could be calcined, then treated with a promoter, and used directly for oxidation of olefin feed or treated with a promoter and then calcined.

Prior to catalyst evaluation (and either before or after further treatment with promoter), all catalysts were optionally calcined in an oxygen-containing atmosphere (air or oxygen-supplemented helium) at about 350° C. for about 4 hours. Following calcination, all catalysts were subjected to an activation treatment at a temperature in the range of about 300°-350° C. in an atmosphere initially containing about 2-5% hydrogen in an inert carrier such as helium or nitrogen. The hydrogen content of the activating atmosphere was gradually increased up to a final hydrogen concentration of about 20-25% at a controlled rate so that the activation temperature did not exceed 350° C. After the temperature was maintained for about 1 hour at a hydrogen concentration in the range of about 20-25%, catalyst was ready for use.

TABLE I

| Alumina-Supported Catalysts | | |
|---|---|---|
| Catalyst | Silver Loading, wt % (Silver Source) | Support |
| A | 1.4 ($AgNO_3$) | $Al_2O_3$[1] |
| B | 5.3 ($AgNO_3$) | $Al_2O_3$[1] |
| C | 12 ($AgNO_3$) | $Al_2O_3$[2] |
| D | 15 ($AgNO_3$) | $Al_2O_3$[2] |
| E | 15 ($AgNO_3$) | $Al_2O_3$[1] |
| F | 25 ($AgNO_3$) | $Al_2O_3$[1] |

[1] catalyst support employed was a fluidizable powder having a surface area of 0.26 $m^2/g$, a total pore volume of 0.675 cc (Hg)/gm, median pore diameter 19$\mu$, a packing density of 0.98 $g/cm^3$, and a chemical composition (wt %) as follows: $Al_2O_3$ - 84.7, $SiO_2$ - 13.4, $Fe_2O_3$ - 0.21, $TiO_2$ - 0.47, CaO - 0.21, MgO - 0.12, $Na_2O$ - 0.15, $K_2O$ - 0.26)

[2] ¼" rings (surface area 0.43 $m^2/g$, total pore volume 0.37 cc (Hg)/gm, median pore diameter 7$\mu$, packing density 0.80 $g/cm^3$, chemical composition (wt %): $Al_2O_3$ - 93.1, $SiO_2$ - 5.6, $Fe_2O_3$ - 0.3, $TiO_2$ - 0.1, CaO - 0.1, MgO - 0.3, $Na_2O$ - 0.1, $K_2O$ - 0.1)

When the $Ag/Al_2O_3$ catalyst was treated with promoter, a quantity of catalyst was contacted with 1-2 volumes of aqueous promoter, then dried as previously described.

When the above-described catalysts have been treated with promoter, such treatment is noted by flagging the catalyst designation with a 'prime' superscript, e.g., A', B' or the like.

Silver was deposited on other supports as well, following the same general procedure as above. Thus, 15.4% Ag on ZnO was prepared by dissolving 9.5 g of $AgNO_3$ in 75 mL of distilled water, then adding to the solution 25 g of uncalcined ZnO (having a surface area of 3.9 $m^2/g$, and a particle diameter in the range of about 75-150$\mu$). This material was then dried as described above and is designated as Catalyst G.

Titania supported catalyst was prepared by calcining $TiO_2$ (having a surface area of about 0.5 $m^2/g$, a particle diameter in the range of about 40-75$\mu$) in oxygen at 450° for about 4 hours. Twenty-five grams of this treated $TiO_2$ was then slurried in about 25 mL of distilled water, to which was added a solution of about 25 mL of distilled water containing 9.5 g of $AgNO_3$. The combination was thoroughly mixed, then dried as described above. The resulting catalyst, containing 17.8% Ag, is designated as Catalyst H.

A boron nitride (BN) supported catalyst was prepared in accordance with the standard procedure set forth above. The BN support was contacted with the necessary amount of aqueous silver nitrate to achieve a 5.3 wt % Ag on BN support catalyst. After soaking for about 30 minutes, water was removed on a rotary evaporator, catalyst dried in air at 120° C., and calcined in an oxygen-containing atmosphere at about 350° C. for 4 hours. After calcination, the catalyst was promoted with an aqueous solution of cesium nitrate to give a final composition containing 1 mg of cesium nitrate per gram of supported catalyst. Catalyst was loaded into a reactor for in situ activation, by reduction for 1 hr. at 350° C. in a stream of 20% $H_2$/80% He. This catalyst is designated as Catalyst I.

EXAMPLE 2

Effect of Silver Loading Level

In all of the following catalyst evaluation runs, catalysts were evaluated under steady state conditions in a 1 atmosphere flow reactor system.

All catalysts were evaluated at steady-state conditions using a one atm, single-pass flow reactor. The reactor tube was constructed of pyrex and the catalyst charge (between 0.1 and 10.0 g) was held in place by means of a pyrex frit. The geometries of the reactor and catalyst particles as well as bed depth were chosen to maintain and measure the true kinetic and catalytic aspects of the reaction. A chromel/alumel thermocouple sheathed in stainless steel was embedded within the catalyst bed to measure the true reaction temperature.

The feed gas $O_2$, as well as the diluent He, were added using mass flow controllers, which permitted highly accurate and reproducible flow rates of $O_2$, and He regardless of pressure changes from the supply cylinders or the reactor system downstream from the controllers.

Styrene was added by passing the helium diluent through a styrene vapor-liquid saturator maintained at a temperature of about 45° C. (or, in some cases, at about 65° C.) and at 1 atm total pressure. The $O_2$ feed gas and styrene saturated helium vapor were mixed in a manifold and passed over the catalyst.

Reaction product analyses (as well as feed composition analyses) were made using an in-line gas sampling loop connected directly to the inlet of a Varian 3760 gas chromatograph. Both thermal conductivity (TC) and flame ionization (FI) detectors [connected in series below the packed Chromosorb 101 column (8 ft. by 2 mm id pyrex capillary column)] were used to analyze all of the reaction products. The TC detector gave quantitative analyses for $O_2$, $CO_2$, $H_2O$, and HCHO (if present), while the FI detector was used for organic molecules such as styrene, styrene oxide, and benzaldehyde. In practice, however, usually only the selective epoxidation product and unconverted unsaturated feedstock were present as organic molecules. Further, by means of a switching valve, it was possible to divert the feed stream through the in-line sample loop prior to passage over the catalyst. In this way, quantitative analysis of the feed stream and comparison to the corresponding data from the reactor effluent were possible, thereby providing very accurate measurements of both conversion levels and product selectivities. Output from both the TC and FI detectors were integrated using computing integrators which were programmed to give both absolute quantities and rates of formation. All reactor exit lines were heated and maintained at 125°–140° C. to prevent product condensation.

The GC analysis was performed using the following temperature programming schedule: an initial temperature of 100° C. was held for 2 minutes, followed by a temperature program rate of +10° C./min up to a final temperature of 220° C. which was then held for 10 minutes. The helium GC carrier rate was 20 mL/min.

In this example, the effect of silver loading level with a 1 mg $CsNO_3$ per gram of finished catalyst promoted $Ag/Al_2O_3$ catalyst on conversion of unsaturated feed and product selectivity at 250° C. was investigated. Reaction parameters and results are presented in Table 2 for reaction of styrene.

TABLE 2

| Catalyst | Ag loading level* (wt %) | Gas Feed** ($He/O_2$/Sty) | Space velocity, ($hr^{-1}$) | Styrene Conversion, % | Product Selectivity, % |
|---|---|---|---|---|---|
| A' | 1.4 | 0.78/0.02/0.20 | 3600 | 0.4 | 59 |
| B' | 5.3 | 0.68/0.02/0.30 | 4200 | 17 | 91 |
| E' | 15 | 0.78/0.02/0.20 | 3600 | 28 | 97 |
|  |  | 0.68/0.02/0.30 | 2100 | 31 | 96 |
| F' | 25 | 0.78/0.02/0.20 | 7200 | 50 | 96 |
|  |  | 0.68/0.02/0.30 | 9000 | 73 | 94 |
| unsupported |  | 0.68/0.02/0.30 | 1050 | 0.6 | 75 |

*All catalysts treated with 1 mg $CsNO_3$ per gram of finished catalyst.
**Volumetric ratio.

The above results demonstrate that high catalyst activity and selectivity are obtained with both unsupported cesium nitrate promoted silver, and supported cesium nitrate promoted silver catalysts over a wide range of silver loading levels on the catalyst support. As one might expect, higher activities are obtained at higher silver loading levels. It is of note that selectivity is not adversely affected even at increasing styrene conversion levels.

EXAMPLE 3

Effect of Adding Various Promoters

A series of catalyst evaluations were carried out employing the same experimental setup described in Example 2. A variety of promoted catalysts were tested for the oxidation of styrene, with reaction parameters and results set forth in Table 3.

TABLE 3

| Cat. | Silver Loading, wt % | Promoter (loading, mg/g*) | Temp, °C. | Gas Feed** He/Sty/$O_2$ | Space Velocity, $hr^{-1}$ | Styrene Conv., % | Product Selectivity, % |
|---|---|---|---|---|---|---|---|
| C | 12 | — | 250 | 0.78/0.02/0.20 | 1200 | 0 | 0 |
|  |  |  | 250 | 0.68/0.02/0.30 | 1200 | 0 | 0 |
| C' | 12 | CsCl(0.5) | 250 | 0.89/0.01/0.10 | 550 | 24 | 84 |
|  |  |  | 225 | 0.89/0.01/0.10 | 550 | 20 | 91 |
| C' | 12 | CsCl(1.0) | 250 | 0.79/0.01/0.20 | 1440 | 23 | 92 |
|  |  |  | 225 | 0.89/0.01/0.10 | 1320 | 36 | 95 |
|  |  |  | 225 | 0.79/0.01/0.20 | 360 | 59 | 92 |
|  |  |  | 200 | 0.79/0.01/0.20 | 360 | 25 | 98 |
|  |  |  | 260 | 0.89/0.01/0.10 | 1320 | 76 | 80 |
|  |  |  | 250 | 0.69/0.01/0.30 | 1900 | 48 | 94 |
| C' | 12 | RbCl(0.72) | 250 | 0.79/0.01/0.20 | 1200 | 16 | 84 |
| D' | 15 | CsCl(1.0) | 250 | 0.91/0.01/0.08 | 330 | 29 | 85 |
|  |  |  | 250 | 0.94/0.01/0.05 | 1050 | 24 | 88 |
|  |  |  | 250 | 0.97/0.01/0.02 | 1050 | 13 | 92 |
|  |  |  | 250 | 0.94/0.01/0.05 | 1200 | 18 | 93 |
|  |  |  | 250 | 0.89/0.01/0.10 | 1200 | 25 | 93 |
| E | 15 | — | 250 | 0.78/0.02/0.20 | 3600 | 0 | 0 |
| E' | 15 | $KNO_3$(1.8) | 250 | 0.66/0.04/0.30 | 1000 | 5 | 34 |
| E' | 15 | $KNO_3$(3.6) | 250 | 0.68/0.02/0.30 | 2100 | 10 | 84 |
| E' | 15 | $Ba(NO_3)_2$(1.55) | 250 | 0.88/0.02/0.10 | 3600 | 3 | 76 |
|  |  |  | 250 | 0.68/0.02/0.30 | 4200 | 7 | 86 |
| E' | 15 | CsCl(1.0) | 250 | 0.88/0.02/0.10 | 3800 | 20 | 95 |
|  |  |  | 250 | 0.91/0.04/0.05 | 3800 | 7 | 94 |
|  |  |  | 250 | 0.86/0.04/0.10 | 3940 | 8 | 95 |
|  |  |  | 250 | 0.76/0.04/0.20 | 4000 | 10 | 95 |
| E' | 15 | CsBr(1.28) | 250 | 0.98/0.02/0.20 | 3600 | 4 | 98 |
| E' | 15 | $CsNO_3$(0.5) | 250 | 0.88/0.02/0.10 | 3500 | 6 | 90 |
| E' | 15 | $CsNO_3$(1.0) | 250 | 0.86/0.04/0.10 | 3600 | 12 | 96 |
|  |  |  | 250 | 0.76/0.04/0.20 | 3600 | 28 | 97 |
|  |  |  | 250 | 0.66/0.04/0.30 | 2100 | 31 | 96 |
|  |  |  | 250 | 0.88/0.02/0.10 | 3600 | 66 | 95 |
| E' | 15 | $CsNO_3$(2.0) | 250 | 0.88/0.02/0.10 | 3500 | 40 | 96 |
| E' | 15 | RbCl(3.0) | 250 | 0.88/0.02/0.10 | 3600 | 4 | 88 |
|  |  |  | 250 | 0.78/0.02/0.20 | 3600 | 19 | 92 |

TABLE 3-continued

| Cat. | Silver Loading, wt % | Promoter (loading, mg/g*) | Temp, °C. | Gas Feed** He/Sty/O$_2$ | Space Velocity, hr$^{-1}$ | Styrene Conv., % | Product Selectivity, % |
|---|---|---|---|---|---|---|---|
|   |   |   | 250 | 0.68/0.02/0.30 | 3600 | 34 | 93 |
| E' | 15 | RbNO$_3$(0.75) | 250 | 0.88/0.02/0.10 | 3300 | 1 | 44 |
| E' | 15 | RbNO$_3$(1.5) | 250 | 0.88/0.02/0.10 | 3300 | 5 | 74 |
| E' | 15 | RbNO$_3$(3.0) | 250 | 0.93/0.02/0.05 | 3450 | 20 | 94 |
|   |   |   | 250 | 0.88/0.02/0.10 | 3600 | 26 | 96 |
|   |   |   | 250 | 0.78/0.02/0.20 | 3600 | 31 | 96 |
|   |   |   | 250 | 0.68/0.02/0.30 | 3600 | 33 | 97 |
| E' | 15 | RbNO$_3$(4.5) | 250 | 0.88/0.02/0.10 | 3600 | 12 | 97 |
|   |   |   | 250 | 0.78/0.02/0.20 | 3600 | 13 | 98 |
|   |   |   | 250 | 0.68/0.02/0.30 | 3600 | 15 | 98 |
|   |   |   | 259 | 0.60/0.04/0.30 | 3600 | 7 | 99 |

*mg of promotor per gram of finished catalyst. Promoter was applied to catalyst as described in Example 1.
**Volumetric ratio These results demonstrate that alkali metal and alkaline earth metal compounds increase the rate of styrene oxide formation and/or increase the selectivity to the desired product (relative to that obtained with unpromoted catalyst), with both rate and selectivity frequently being improved.

The benefit of these additives is also observed to be independent of the silver loading on the support.

EXAMPLE 4

Comparison Catalyst—BaO$_2$ Promoted Silver Catalyst

Catalyst (F$_1$) as described by Y. Murakami and K. Tanaka in Nippon Kagaku Kaishi, Vol. 11, p. 1603 (1977) was prepared to test for styrene oxidation activity.

Sufficient quantity of aqueous NaOH (10 g NaOH in 25 mL water) was added to a solution of 3.31 g of AgNO$_3$ in 20 mL of water until no further Ag$_2$O precipitate was formed. The freshly precipitated Ag$_2$O was thoroughly washed to remove residual quantities of sodium and nitrate ions.

Powdered alumina support (see Footnote 1 of Table I above; 7.5 g) was slurried in 20 mL of distilled water. To this slurry, a second slurry containing 2.1 g of freshly prepared Ag$_2$O and 0.4 g of BaO$_2$ in 25 mL of distilled water was added. After rotary evaporation at 60° C. and oven drying at 110° C., the resulting catalyst was determined by neutron activation analysis to have a composition comprising 20 wt % silver and 4.2 wt % barium. Results of styrene oxidation with this catalyst and invention catalysts are compared in Table 4. All reactions were carried out at 250° C., unless otherwise noted.

TABLE 4

| Catalyst | Silver Loading, % | Promoter (loading, mg/g)* | Gas Feed (He/Sty/O$_2$)** | Space Velocity, (hr$^{-1}$) | Styrene Conversion, | Product Yield |
|---|---|---|---|---|---|---|
| Comparison | 20 | BaO$_2$(51.8)**** | 0.68/0.02/0.30 | 2100 | 2 | 57 |
|   |   |   | 0.68/0.20/0.3*** | 2100 | 6 | 50 |
| E' | 15 | Ba(NO$_3$)$_2$(1.55) | 0.88/0.02/0.10 | 3300 | 3 | 76 |
|   |   |   | 0.68/0.02/0.30 | 1050 | 6 | 57 |
|   |   |   | 0.68/0.02/0.30 | 4200 | 7 | 86 |

*mg of promoter per gram of finished catalyst.
**Volumetric ratio.
***Run at 273° C.
****A loading of 51.8 mg BaO$_2$ per gram of finished catalyst corresponds to 4.2% (by weight) of Ba, as determined by neutron activation analysis.

The results in Table 4 demonstrate that the BaO$_2$ promoted catalyst disclosed by Murakami et al is not as effective (either in terms of conversion or selectivity) as are barium promoted catalysts of the present invention for the selective oxidation of styrene to produce styrene oxide.

A further comparison of results set forth in Table 3 with the results in Table 4 demonstrates that the alkali metal promoters are preferred relative to alkaline earth metal compounds. In particular, compounds of cesium are especially preferred promoters for the preparation of catalysts of the present invention.

EXAMPLE 5

Effect of Various Catalyst Supports

A series of catalyst evaluations were carried out employing the same experimental setup described in Example 2. A variety of supported catalysts, prepared using different catalyst supports, were tested. The reaction parameters and results are set forth in Table 5. All reactions were carried out at 250° C.

TABLE 5

|   | Reaction Parameters | | | | |
|---|---|---|---|---|---|
| Catalyst | Promoter, (loading level, mg/g)* | Feed** (He/Sty/O$_2$) | Space Velocity, hr$^{-1}$ | Styrene Conversion, % | Product Selectivity, % |
| G' | CsNO$_3$(1.0) | 0.88/0.02/0.10 | 3600 | 10 | 89 |
| G' | CsNO$_3$(1.0) | 0.68/0.02/0.30 | 2100 | 22 | 85 |
| G' | CsNO$_3$(1.0) | 0.68/0.02/0.30 | 4200 | 23 | 91 |
| H' | CsNO$_3$(3.0) | 0.88/0.02/0.10 | 3600 | 3 | 85 |
|   |   | 0.78/0.02/0.20 | 3600 | 5 | 92 |
|   |   | 0.68/0.02/0.30 | 3600 | 7 | 95 |
| I' | CsNO$_3$(1.0) | 0.68/0.02/0.30 | 2800 | 3 | 55 |
|   |   | 0.68/0.02/0.30 | 5600 | 2 | 80 |

*mg of promoter per gram of finished catalyst.
**Volumetric ratio.

These results demonstrate that a variety of supports are effective for the highly selective conversion of styrene to stryene oxide. The results also indicate that alumina is the presently preferred support for use in the practice of the present invention.

EXAMPLE 6

Selective Epoxidation of a Variety of Styrene Derivatives

The same experimental set-up described in Example 2 was employed with divinylbenzene, p-chloro styrene, p-fluoro styrene and p-methyl styrene as the reactive feed. Catalyst E, promoted with 1 mg $CsNO_3$ per gram of finished catalyst was used for all these evaluations. Reaction parameters and results are set forth in Table 6.

TABLE 6

Selective Oxidation of Vinyl Benzene Derivatives (VBD)

| Vinyl Benzene Derivative | Reaction Temp., °C. | Feed (He/VBD/$O_2$) | Space Velocity, $hr^{-1}$ | VBD Conversion, % | Product* Selectivity, % |
|---|---|---|---|---|---|
| Divinylbenzene | 265 | 0.49/0.01/0.50 | 800 | 7.2 | 71 |
| p-Chlorostyrene | 264 | 0.66/0.01/0.33 | 820 | 2.7 | 62 |
| p-Fluorostyrene | 250 | 0.42/0.08/0.50 | 550 | 1.3 | 86 |
| p-Methylstyrene | 225 | 0.87/0.01/0.12 | 560 | 100 | 0** |

*Desired product is the monoepoxide
**Essentially quantitative yield of $CO_2$ and $H_2O$ These results demonstrate that aryl-vinyl compounds having no allylic hydrogens, e.g., divinylbenzene, p-chlorostyrene and p-fluorostyrene can be selectively oxidized to the mono-epoxide derivative according to the practice of the present invention. The results with p-methylstyrene, a compound not within the scope of the present invention, demonstrates that selective oxidation is not possible with a closely related styrene derivative which contains allylic hydrogens.

EXAMPLE 7

Selective Epoxidation of 4-Vinyl-Pyridine

The oxidation of 4-vinyl pyridine was carried out employing the same experimental setup described in Example 2. The catalyst employed was 12% silver on alumina (Catalyst C, see Table I) promoted with 1.0 mg per gram of catalyst of CsCl and 0.31 mg per gram of catalyst of $CsNO_3$ (promoters added as described in Example 1).

4-Vinyl pyridine was introduced into the reactor by passing the helium diluent through a 4-vinyl pyridine liquid-vapor saturator maintained at about 70° C. When the 4-vinyl pyridine-containing helium gas stream and oxygen-containing gas stream were combined, a feed gas composition was obtained having a volumetric ratio of helium/4-vinyl pyridine/oxygen of 0.89:0.04:0.11.

Following the procedure set forth in Example 2, at a reaction temperature of about 246° C. and a gas hourly space velocity (GHSV) of about 250 $hr^{-1}$, the conversion of 4-vinyl pyridine was 21.4%, with a molar selectivity to 4-vinyl pyridine epoxide of about 86%. The remainder of the reacted 4-vinyl pyridine was accounted for as $CO_2$.

These results demonstrate that the invention oxidation reaction is effective for the selective oxidation of 4-vinyl pyridine to 4-vinyl pyridine epoxide.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

We claim:

1. Process for the selective monoepoxidation of aryl-vinyl compounds having the structure:

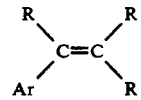

wherein Ar is phenyl; phenyl substituted with methyl, methoxy, halogen, vinyl, or phenyl; naphthyl; or pyridyl; and each R is independently selected from hydrogen and alkyl having in the range of 1 up to 20 carbon atoms, with the proviso that there are no hydrogen atoms allylic to a double bond in said structure;

said process comprising contacting said aryl-vinyl compound with a sufficient quantity of an oxygen-containing gas so as to maintain the molar ratio of aryl-vinyl compound to oxygen in the range of 0.01 to up to 30, in the presence of a silver-containing catalyst containing in the range of 0.01 to 2 weight %, based on the total weight of catalyst, including support, of at least one promoter selected from the salts and oxides of cesium and rubidium; wherein said contacting is carried out at a pressure in the range of 0.1 up to 100 atmospheres, at a temperature in the range of 100° up to 325° C. for a time sufficient to obtain aryl-vinyl compound conversions in the range of 0.5 up to 75%.

2. Process in accordance with claim 1 wherein said silver catalyst comprises (i) about 1-30 weight percent silver, (ii) about 0.01 to 2 weight percent of a promoter selected from a halide or nitrate of cesium or rubidium, and (iii) an alumina support having a surface area of less than about 10 $m^2/g$; wherein said weight percentages are based on the total weight of the catalyst.

3. Process in accordance with claim 2 wherein the promoter is selected from the group consisting of cesium chloride, cesium bromide, cesium nitrate and mixtures thereof.

4. Process in accordance with claim 2 wherein the promoter is selected from the group consisting of rubidium chloride, rubidium bromide, rubidium nitrate and mixtures thereof.

5. Process in accordance with claim 2 wherein said contacting is carried out at a temperature of about 175° to 275° C., at a pressure of about 1 to 30 atmospheres, and for a time sufficient to obtain aryl-vinyl compound conversions of about 5 to 60%.

6. Process for the selective epoxidation of an aryl-vinyl compound selected from the styrene, divinyl benzene and 4-vinylpyridine which comprises contacting said aryl-vinyl compound with a sufficient quantity of an oxygen-containing gas so as to maintain the molar ratio of aryl-vinyl compound to oxygen in the range of 0.01 up to 30, in the presence of a silver-containing catalyst comprising (1) about 2 to 20 weight percent silver, (2) about 0.01 to 2 weight percent of an alkali metal halide or nitrite selected from the group consisting of cesium chloride, cesium bromide, cesium nitrate, and mixtures thereof, and (3) an alumina support having a surface area of less than about 1 $m^2/g$, wherein said weight percentages are based on the total weight of the catalyst; wherein said contacting is carried out at a pressure of 1 to 30 atmospheres and at a temperature of 175° to 275° C.

* * * * *